United States Patent [19]

Vargas et al.

[11] 4,261,358

[45] Apr. 14, 1981

[54] AUTOMATIC SYRINGE PLUNGER

[76] Inventors: Walter Vargas, c/o George Spector 3615 Woolworth Bldg. 233 Broadway; George Spector, 3615 Woolworth Bldg., 233 Broadway, both of New York, N.Y. 10007

[21] Appl. No.: 80,179

[22] Filed: Oct. 1, 1979

[51] Int. Cl.³ .............................................. A61M 5/22
[52] U.S. Cl. ................................................. 128/218 F
[58] Field of Search ........... 128/218 F, 218 R, 218 A, 128/234

[56] References Cited

U.S. PATENT DOCUMENTS

| 2,531,267 | 11/1950 | Harnisch | 128/218 F |
| 2,632,445 | 3/1953 | Kas, Sr. | 128/218 F |
| 2,671,448 | 3/1954 | Harnisch | 128/218 F |
| 3,702,608 | 11/1972 | Tibbs | 128/218 F |

Primary Examiner—John D. Yasko

[57] ABSTRACT

A hypodermic needle for overcoming a patient's fear of the needle puncture; the device including a latch mechanism that is tripped so to free a compressed spring that instantly drives a hidden-from-view needle into the flesh.

3 Claims, 2 Drawing Figures

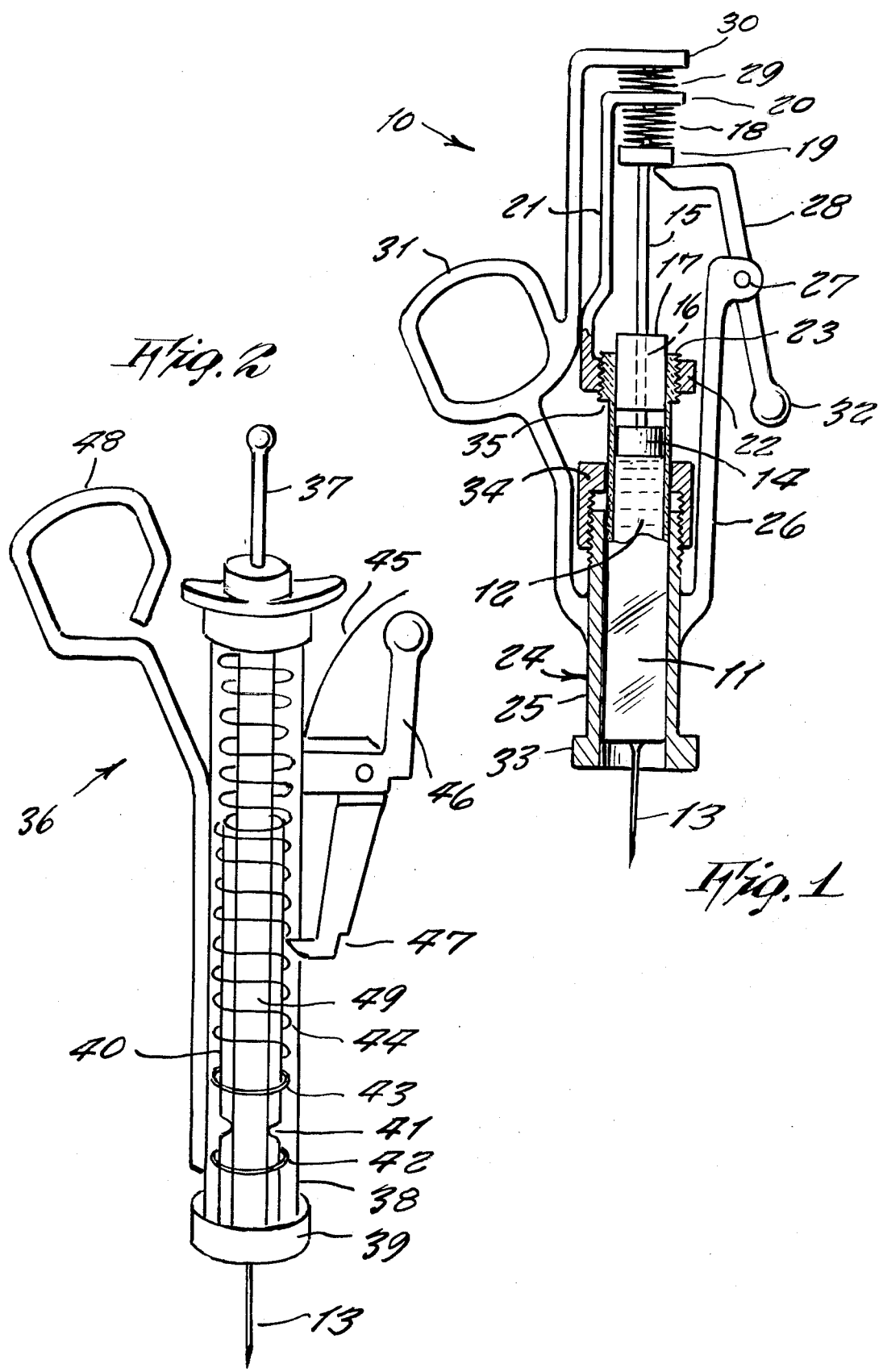

AUTOMATIC SYRINGE PLUNGER

This invention relates generally to hypodermic needles.

It is well known that most person are afraid or at least apprehensive of receiving a puncture from a hypodermic needle. When it is administered by a physician, most persons find it impossible to bear looking at the needle while being pushed into the flesh. This situation is even worse for those who must administer their own injections, such as diabetic patients and others who regularly require medication. This situation is accordingly in need of an improvement.

Therefore, it is a principal object of the present invention to provide an automatic syringe plunger which hides the needle from view during insertion into the flesh so to overcome the apprehension and fear thereof by patients, particularly those who take their own injections.

Another object is to provide an automatic syringe plunger which drives the needle into the flesh at a fast speed so that it is less uncomfortable in piercing through the skin.

IN THE DRAWING

FIG. 1 is a cross sectional elevation of the invention.

FIG. 2 is a perspective view of another form of the invention.

Referring now to the drawing in greater detail, and more particularly to FIG. 1 thereof at this time, the reference numeral 10 represents an automatic syringe plunger according to the present invention wherein there is a vial or plastic syringe 11 containing a medication 12, the syringe being integral with injection needle 13. A plunger 14 inside the syringe is integral with rod 15 slidable in a hole 16 of an end cap 17 fitted in an end of the syringe.

A compression coil spring 18 bears at one end against a pressure plate 19 formed on the end of rod 15 so as to urge the medication from the syringe outwardly through the needle. The spring 18 bears at its other end against a pressure plate 20 integral, by means of bar 21, with a threaded ring 22 screwed on a threaded neck 23 of the syringe.

A rigid housing 24 includes tubing 25 inside which the syringe is slided. An arm 26 integral with the housing carries a pivot pin 27 about which a cocking latch lever 28 is pivotable. One end of the lever bears against the underside of plate 19 when in a cocked position as shown in FIG. 1, preventing the spring 18 to force the plunger against the medication.

A second compression coil spring 29 is between the pressure plate 20 and a pressure plate 30 that is integral with the housing 25.

A ring handle 31 is formed on the housing, and a rounded knob 32 is formed on an opposite end of the latch lever; the handle and knob being on opposite sides of the implement so as to be squeezed in a hand when the device is used.

In operative use, the implement is first loaded with a medication-filled syringe by screwing the syringe neck 23 into the ring 23. The pressure plates 19 and 20 are upwardly urged so as to compress the springs 18 and 29. The latch lever 28 is then pivoted to bear against underside of plate 19, so that the latch lever in cocked position, as shown in FIG. 1, holds both springs in compressed condition.

After positioning the needle at proper location to penetrate the skin, the knob and handle are squeezed together, causing the latch lever to slide out from under the plate 19 thus freeing the spring 29 to thrust the needle into the flesh and at the same time cause the spring 18 to force the plunger to push the medication out of the needle.

It will be noted that a wide flange 13 around the base of the housing hides the needle from ready view during the skin penetration.

A stop collar 34 screwed on the housing is abutted by a shoulder 35 of the syringe neck so to limit the depth of needle penetration.

The thread engagement of ring 22 on the neck allows adjustment of compression for both springs.

In FIG. 2 another design of automatic syringe plunger 36 utilizes a V-100, disposable type syringe model which is most commonly used today.

The device includes a syringe plunger 37, a housing tubing 38, threaded cap 39, a syringe carrier tube 40, grip notch 41, stabilizer washer 42, (spring carrier) fixed washer 43, shooting spring 44, cocking spring 45, latch mount 46, cocking latch 47 and handle 48.

The automatic syringe plunger 36 is operated by a V-100 model plastic syringe 49 being inserted through the top opening and being pushed all the way in. It will be held firm by the notch grip 41. The syringe is pulled up and it will carry the syringe carrier tube 40 with it. The (spring carrier) fixed washer 43 will cock onto the cocking latch 47, and the syringe will shoot downwardly when the knob on the latch mount 46 is depressed.

In order to remove the used-up syringe, it can be easily pulled out by applying a small force thereagainst.

What is claimed as new is:

1. An automatic syringe plunger assembly, comprising in combination, a housing having a tubing portion inside which a syringe containing medication is inserted, said syringe including an inoculation needle at one end, a handle on one side of said housing a cocking latch on a lever at an opposite side of said housing and a knob on an end of said lever for being squeezed in a hand together with said handle, and spring means held in cocked position by said latch said spring means being aligned respective to said syringe so as to slide said syringe and needle respective to said housing wherein said spring means comprises a first and second compression coil springs axially aligned, a first pressure plate adjacent one end of said first spring being integral with a plunger in said syringe, a second pressure plate between said springs being adjustably affixed to said syringe, and a third pressure plate adjacent one end of said second spring being integral with said housing said cocking latch bearing against said first pressure plate against an action of said compression springs.

2. The combination as set forth in claim 1, wherein said spring means includes a compression coil spring bearing at one end against said housing, said syringe being grasped inside a syringe carrier tube inside said spring, a fixed washer on an opposite end of said spring being hooked on said cocking latch when said spring is forcibly compressed.

3. The combination as set forth in claim 2 wherein a grip notch is provided along said syringe carrier tube, said grip notch extending radially inwardly for fractionally grasping said syringe.

* * * * *